(12) United States Patent
Treacy et al.

(10) Patent No.: US 9,526,605 B2
(45) Date of Patent: Dec. 27, 2016

(54) MULTI VALVE ANTI-REFLUX PROSTHESIS

(71) Applicant: Cook Medical Technologies LLC, Bloomington, IN (US)

(72) Inventors: Gerard Treacy, Castletroy (IE); Michael Ryan, Dooradoyle (IE); Alison Liddy, Salthill (IE); John Neilan, Gort (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/149,104

(22) Filed: Jan. 7, 2014

(65) Prior Publication Data

US 2014/0195006 A1 Jul. 10, 2014

Related U.S. Application Data

(60) Provisional application No. 61/750,183, filed on Jan. 8, 2013.

(51) Int. Cl.
*A61F 2/04* (2013.01)
*A61F 2/24* (2006.01)

(52) U.S. Cl.
CPC ............... *A61F 2/04* (2013.01); *A61F 2/2475* (2013.01); *A61F 2002/044* (2013.01)

(58) Field of Classification Search
CPC .......................... A61F 2002/044; A61F 2/2475
USPC .............. 623/1.24–1.26, 23.64, 23.67, 23.68
See application file for complete search history.

(56) References Cited

U.S. PATENT DOCUMENTS

| 4,434,810 A | 3/1984 | Atkinson |
|---|---|---|
| 4,846,836 A | 7/1989 | Reich |
| 5,314,473 A | 5/1994 | Godin |
| 5,392,775 A | 2/1995 | Adkins, Jr. et al. |
| 5,861,036 A | 1/1999 | Godin |
| 6,264,700 B1 | 7/2001 | Kilcoyne et al. |
| 6,302,917 B1 | 10/2001 | Dua et al. |
| 6,544,291 B2 | 4/2003 | Taylor |
| 6,746,489 B2 | 6/2004 | Dua |
| 6,790,237 B2 | 9/2004 | Stinson |
| 7,118,600 B2 | 10/2006 | Dua et al. |

(Continued)

FOREIGN PATENT DOCUMENTS

| EP | 1 430 853 B1 | 6/2004 |
|---|---|---|
| EP | 1 704 834 B1 | 9/2006 |

(Continued)

*Primary Examiner* — Thomas J Sweet
*Assistant Examiner* — Daniel Bissing
(74) *Attorney, Agent, or Firm* — Brinks Gilson & Lione (57) ABSTRACT

A prosthesis and a method of controlling flow through a bodily lumen are provided. The prosthesis includes a body having a proximal portion, a distal portion and a lumen extending therethrough. The prosthesis also includes a first valve and a second valve operably connected to the body. The first valve has a proximal portion, a distal portion, a distal end extending distally relative to the proximal portion of the body and a lumen extending through the first valve. The first valve is closed in the absence of a second and third pressure that are greater than a first pressure. The second valve has a proximal portion, a distal portion, a distal end extending distally relative to a proximal portion of the body and a lumen extending through the second valve, the distal end of the first valve extending distal to the distal end of the second valve.

19 Claims, 8 Drawing Sheets

(56) References Cited

U.S. PATENT DOCUMENTS

| | | |
|---|---|---|
| 7,182,788 B2 | 2/2007 | Jung et al. |
| 7,354,455 B2 | 4/2008 | Stinson |
| 7,993,410 B2 | 8/2011 | Shin et al. |
| 8,029,557 B2 | 10/2011 | Sobrino-Serrano et al. |
| 8,221,505 B2 | 7/2012 | Skerven |
| 2003/0040808 A1 | 2/2003 | Stack et al. |
| 2004/0102855 A1 | 5/2004 | Shank |
| 2005/0027348 A1* | 2/2005 | Case .................. A61F 2/2412 623/1.24 |
| 2005/0137681 A1 | 6/2005 | Shoemaker et al. |
| 2007/0027535 A1* | 2/2007 | Purdy et al. .................. 623/2.18 |
| 2007/0213813 A1 | 9/2007 | Von Segesser et al. |
| 2008/0086214 A1 | 4/2008 | Hardin et al. |
| 2009/0138071 A1 | 5/2009 | Cheng et al. |
| 2009/0171447 A1 | 7/2009 | Von Segesser et al. |
| 2010/0036504 A1 | 2/2010 | Sobrino-Serrano et al. |
| 2010/0114327 A1 | 5/2010 | Sobrino-Serrano |
| 2010/0121461 A1 | 5/2010 | Sobrino-Serrano et al. |
| 2010/0121462 A1 | 5/2010 | Sobrino-Serrano et al. |
| 2010/0137998 A1 | 6/2010 | Sobrino-Serrano et al. |
| 2011/0160836 A1 | 6/2011 | Behan |
| 2011/0190905 A1 | 8/2011 | Behan |
| 2012/0059486 A1 | 3/2012 | Sobrino-Serrano et al. |
| 2012/0089236 A1 | 4/2012 | Errico et al. |
| 2012/0158026 A1 | 6/2012 | Behan |
| 2012/0197386 A1 | 8/2012 | Von Segesser et al. |

FOREIGN PATENT DOCUMENTS

| | | |
|---|---|---|
| EP | 1 952 785 B1 | 8/2008 |
| EP | 2 248 486 A2 | 11/2010 |
| EP | 2 316 381 A2 | 5/2011 |
| EP | 2 368 527 A1 | 9/2011 |
| EP | 2 387 973 A1 | 11/2011 |
| GB | 1 354 691 A | 5/1974 |
| WO | WO 01/66190 A2 | 9/2001 |
| WO | WO 03/030782 A1 | 4/2003 |
| WO | WO 2005/011534 A1 | 2/2005 |
| WO | WO 2006/004679 A1 | 1/2006 |
| WO | WO 2008/028569 A1 | 3/2008 |
| WO | WO 2011/073970 A1 | 6/2011 |
| WO | WO 2013/144770 A2 | 10/2013 |
| WO | WO 2014/022500 A1 | 2/2014 |

* cited by examiner

MULTI VALVE ANTI-REFLUX PROSTHESIS

RELATED APPLICATIONS

This application claims the benefit of U.S. Provisional Application No. 61/750,183 filed Jan. 8, 2013, which is incorporated herein in its entirety.

FIELD OF THE INVENTION

The present invention relates to medical devices and in particular to a prosthesis having multiple valves for regulating fluid flow therethrough.

BACKGROUND OF THE INVENTION

The lower esophageal sphincter (LES) in healthy individuals allows food to pass into the stomach, but prevents gastric fluids from moving into the esophagus except when the patient vomits. Aspiration and gastroesophageal reflux disease (GERD) are clinical risks for patients having a malfunctioning LES or for patients having stents placed across the LES so that the LES remains open. Aspiration occurs when the stomach contents travel from the stomach into the lungs. Aspiration in the lungs can lead to pneumonia or death. GERD produces heartburn, abdominal pain and regurgitation of the stomach contents into the esophagus and pharynx. GERD may lead to the alteration of the lining of the esophagus that results in Barrett's Esophagus and may progress to esophageal cancer. Risk of aspiration and GERD in patients having a compromised LES increases when the patient is in a prone position.

Anti-reflux esophageal prostheses or stents have been developed to treat tumors or strictures in the vicinity of the LES. An anti-reflux esophageal prosthesis or stent is typically placed in the lower esophagus and through the LES to maintain the patency thereof due to the presence of a cancerous tumor commonly found in the vicinity thereof or to treat benign tumor conditions, such as blockage or strictures.

A problem with an esophageal prosthesis or stent is that fluid from the stomach flows into the mouth of the patient when in a prone position, increasing the risk of aspiration and reflux. In an attempt to solve the problem, a number of esophageal prostheses or stents utilize a one-way valve in which only food or fluid from the esophagus flows into the stomach in only an antegrade or forward direction. However, these one-way anti-reflux prostheses or stents present another problem. When the patient wants to belch or vomit, the patient is prevented from doing so, because the one-way valve prevents backward flow in the retrograde direction. Such a condition is not only painful to the patient, but can also lead to more complicated medical conditions. Other inverting valves can invert with pressure at which the patient coughs or belches that allows some reflux, however, these designs do not readily revert back to the original position.

What is needed is a prosthesis that allows food to pass into the stomach and prevents gastric fluids from entering the esophagus, yet allows for vomiting and belching when necessary.

BRIEF SUMMARY

Accordingly, it is an object of the present invention to provide a device and a method having features that resolve or improve on the above-described drawbacks.

In one aspect, a prosthesis for controlling flow through a bodily lumen is provided. The prosthesis includes a body having a proximal portion, a distal portion and a lumen extending therethrough. The prosthesis also includes a first valve and a second valve operably connected to the body. The first valve has a proximal portion, a distal portion, a distal end extending distally relative to the proximal portion of the body and a lumen extending through the first valve. The first valve is closed in the absence of a second pressure and a third pressure that are greater than a first pressure. The second valve has a proximal portion, a distal portion, a distal end extending distally relative to a proximal portion of the body and a lumen extending through the second valve, the distal end of the first valve extending distal to the distal end of the second valve. The second valve and the first valve control flow through the prosthesis.

In another aspect, a method of controlling flow through a bodily lumen is provided. The method includes positioning a body of a prosthesis within the bodily lumen, the prosthesis including a first valve and a second valve. The method further includes extending a distal end of the first valve distal to a distal end of the second valve and collapsing the distal end of the first valve on itself so that the first valve is closed in the absence of a second pressure and a third pressure that are greater than a first pressure and opening the first valve and the second valve in response to the second pressure so that flow is through the prosthesis in an antegrade direction.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the prosthesis to a patient. Hence the term "distal" means the portion of the prosthesis that is farthest from the physician and the term "proximal" means the portion of the prosthesis that is nearest to the physician.

The present invention relates to medical devices, and in particular to prosthetic devices for implantation in a body lumen such as the lower esophageal sphincter or a vessel. As used herein, the term "implantable" refers to an ability of a medical device to be positioned at a location within a body, such as within a body lumen, either temporarily, semi-permanently, or permanently. Permanent fixation of the device in a particular position is not required. Furthermore, the terms "implantation" and "implanted" refer to the positioning of a medical device at a location within a body, such as within a body lumen.

Figure 1A:
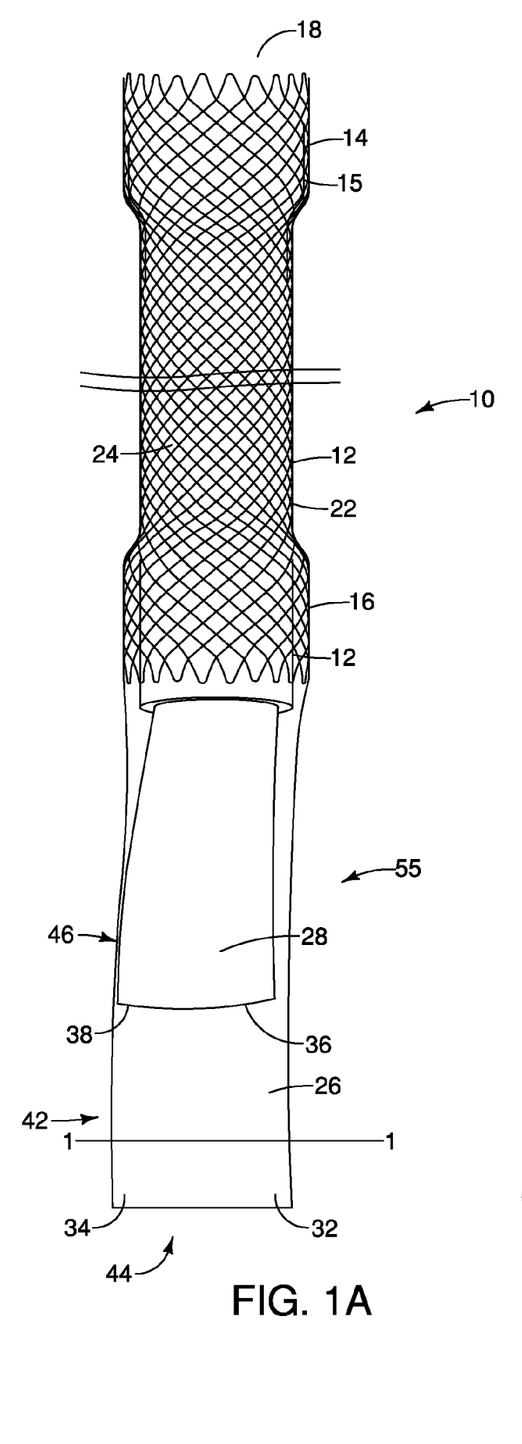
FIG. 1A is a side view of an embodiment of a prosthetic device in accordance with an embodiment of the present invention.

FIG. 1A illustrates a prosthesis 10 in accordance with an embodiment of the present invention. The prosthesis 10 includes a body 12 having proximal portion 14, a distal portion 16 and a lumen 18 extending therethrough. In some embodiments, the body 12 may be an expandable stent, such as a self-expanding stent. Non-limiting examples of expandable stents include the Z-Stent® and the EVOLUTION® stent (Cook Medical, Inc., Bloomington, Ind.). In some embodiments, the body 12 may be a non-expandable tubular stent. The proximal portion 14 may include an end portion 15 having an expanded outer diameter and the distal portion 16 may include an end portion 17 having an expanded outer diameter. The body 12 may include a coating or a sleeve 22 extending through or around the body 12 that is liquid impermeable so that liquid and nutrients flowing from the proximal portion 14 to the distal portion 16 or stomach contents from the distal portion 16 to the proximal portion 14 do not pass through a wall 24 of the body 12. In some embodiments, the prosthesis 10 includes a first valve 26 and a second valve 28. The first valve 26 and the second valve 28 may cooperate to better control the flow through the prosthesis 10 and the sealing of the prosthesis 10 better than a single valve device is able to do. The first valve 26 may be contiguous with the coating or sleeve 22 and in some embodiments the first valve 26 may be separately provided. The first valve 26 and the second valve 28 each control fluid flow through the prosthesis 10. The first valve 26 and the second valve 28 may be provided as flexible sleeves wherein one or more of the sleeve valves may be closable on itself to cooperatively prevent stomach contents from leaking into the mouth through the prosthesis. In some embodiments, the first valve 26 and the second valve 28 may be directly connected to the body 12. In some embodiments, the first valve 26 may be directly connected to the body 12 and the second valve 28 may be connected to the first valve 26 to operably connect to the body 12. Other configurations for operably connecting the first and second valves 26, 28 to the body 12 are also possible.

Figure 1B:
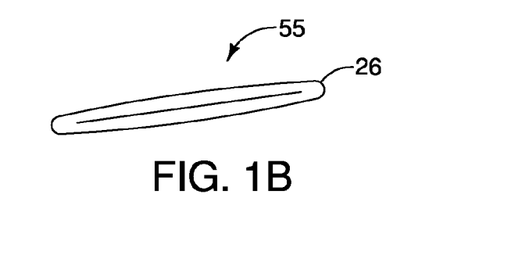
FIG. 1B is a cross sectional view along line 1-1 of FIG. 1A
Figure 2:
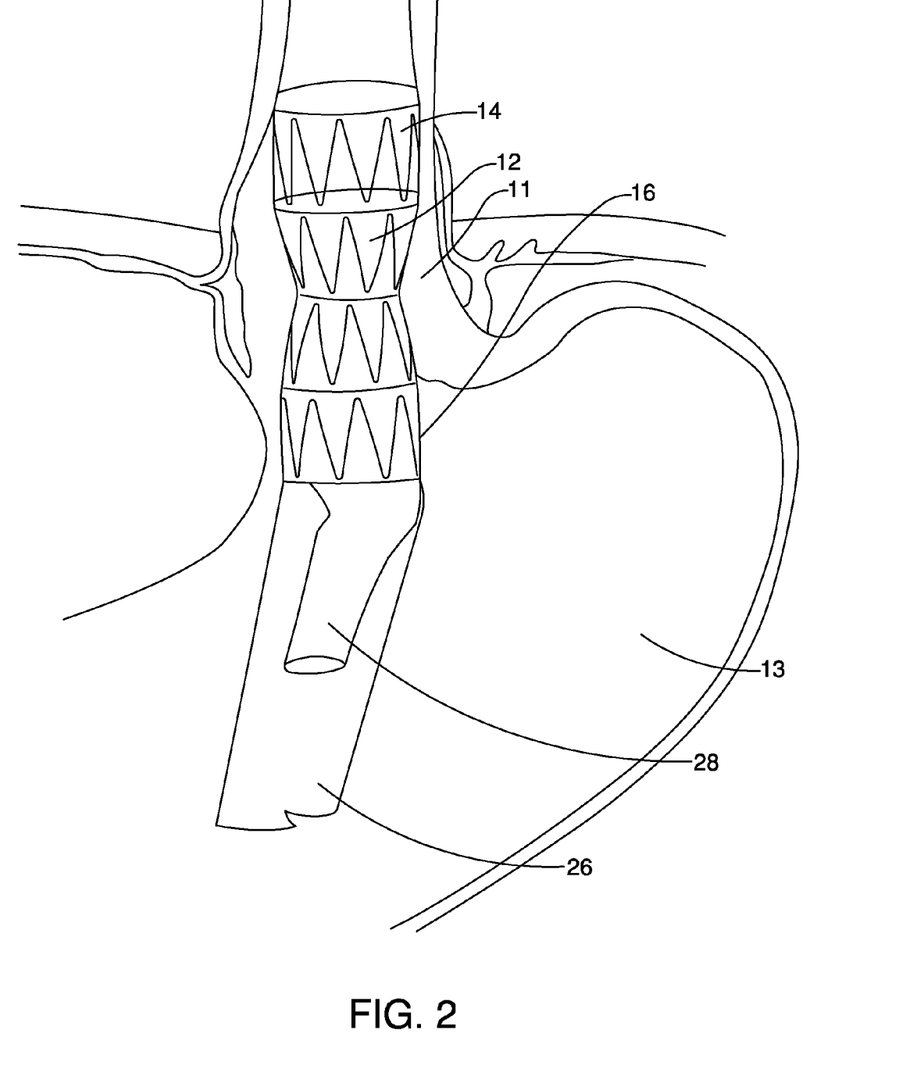
FIG. 2 is an illustration of an embodiment of a prosthetic device positioned in the lower esophageal sphincter of a patient.

As shown in FIG. 2, the prosthesis 10 may be positioned in the lower esophageal sphincter 11. The proximal portion 14 of the body 12 may be positioned proximal to the lower esophageal sphincter 11. The distal portion 16 of the body 12 may be positioned so that the distal portion 16 and the first valve 26 extend into the stomach 13. In some embodiments, the second valve 28 may also extend distal to the distal portion 16 of the body 12 and into the stomach 13. The first valve 26 remains closed in the presence of a first pressure 44 normally present in the stomach 13 so that flow through the prosthesis 10 is substantially prevented as shown in FIG. 1B. The second valve 28 may also remain closed in the presence of the first pressure 44. The first valve 26 and the second valve 28 open in response to a second pressure 48 that occurs when liquid and nutrients flow from the mouth and pass to the stomach 13. The second pressure 48 is greater than the first pressure 44. The first valve 26 and the second valve 28 may open in response to a third pressure 50 that is greater than the first and second pressures 44, 48. For example, when the patient needs to belch or vomit, the valves 26, 28 open in response to the third pressure 50. The third pressure 50 pushes the valves 26, 28 proximally to open the valves 26, 28 so that the third pressure 50 built up in the stomach may be relieved through the mouth as will be explained in more detail below with reference to FIGS. 7-10.

Referring to the embodiment shown in FIG. 1A, the first valve 26 extends distally from the distal portion 16 of the body 12 and the second valve 28 extends distally from the distal portion 16 and within a lumen 32 of the first valve 26. In some embodiments, the second valve 28 extends entirely within the first valve 26 so that a distal end 34 of the first valve 26 is distal to a distal end 36 of the second valve 28. The first valve 26 is operably connected to the body 12 of the prosthesis 10. The second valve 28 is operably connected to the body 12 and may be connected to the body 12 via connection to the first valve 26, for example when the second valve 28 extends entirely within the first valve 26. The second valve 28 includes a lumen 38 that is operably connected to the lumen 18 of the body 12. In some embodiments, the lumen 32 of the first valve 26 may also operably connect to the lumen 18 of the body 12. In some embodiments, only the lumen 38 of the second valve 28 is operably connected to the lumen 18 of the body 12. The lumen 38 of the second valve 28 operably connects to the lumen 32 of the first valve 26 so that liquid and nutrients and stomach contents can flow through the prosthesis 10 in response to the appropriate pressure. A distal end portion 42 of the first valve 26 is normally closed in response to the first pressure 44 so that the distal end portion 42 collapses on itself in the absence of liquid or nutrients flowing from the mouth to the stomach. A distal end portion 46 of the second valve 28 may also be normally closed in response to the first pressure 44 so that the distal end portion 46 collapses on itself. The first valve 26 and the second valve 28 cooperatively prevent leakage of stomach contents through the prosthesis 10 in response to the first pressure 44, especially when the patient is in a prone position. In response to the second pressure 48 that is greater than the first pressure 44, the first and second distal end portions 42, 46 open to allow flow from the mouth to the stomach in a first antegrade direction 49 (shown in FIG. 10). Once the contents have passed from the mouth to the stomach, the first valve 26 and in some embodiments, the second valve 28, return to the closed position. In response to the third pressure 50, the first and second valves 26, 28 invert to relieve the third pressure 50 and flow is in a second retrograde direction 51 as shown in FIGS. 7-10 and described in more detail below.

Figure 3:
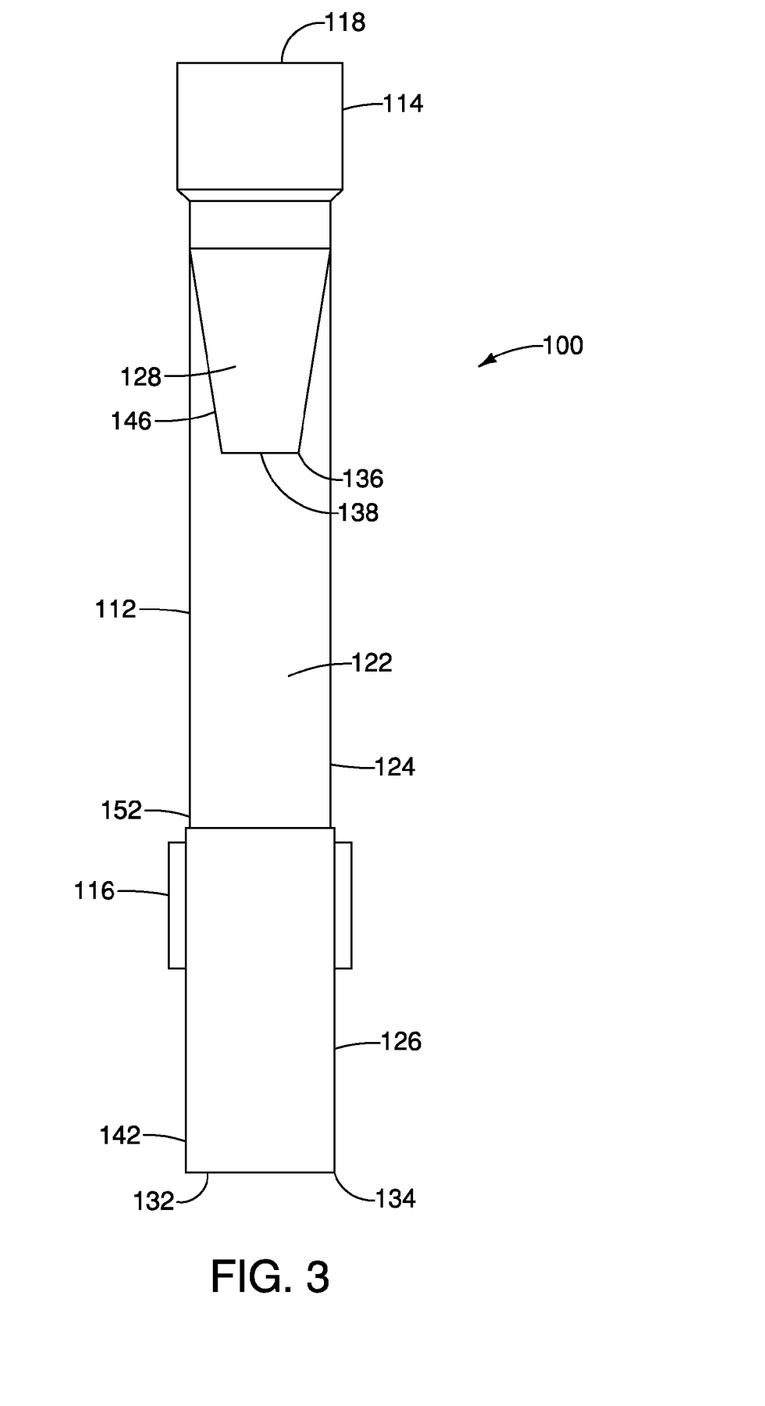
FIG. 3 is a side sectional view of an embodiment of a prosthetic device having a first valve and a second valve.

FIG. 3 illustrates an embodiment of a prosthesis 100. The prosthesis 100 includes a body 112 having proximal portion 114, a distal portion 116 and a lumen 118 extending therethrough. Similar to the prosthesis 10 described above, the prosthesis 100 may include an expandable or a non-expandable stent. The body 112 may include a coating or a valve 122 extending through or around the body 112 that is liquid impermeable so that flow of liquid and nutrients passing from the proximal portion 114 to the distal portion 116 or stomach contents from the distal portion 116 to the proximal portion 114 do not pass through a wall 124 of the body 112. The prosthesis 100 includes a first valve 126 and a second valve 128. In some embodiments, the first valve 126 and the second valve 128 may be provided as flexible sleeves.

As shown in FIG. 3, the first valve 126 extends distally from the distal portion 116 of the body 112 so that a distal end 134 of the first valve 126 extends distal to the distal portion 116 of the body 112. The second valve 128 extends distally from the body 112 and is positioned proximal to the first valve 126. As shown in FIG. 3, the second valve 128 is spaced apart from the first valve 126. The second valve 128 may extend distally such that a distal end 136 of the second valve 128 is entirely within the lumen 118 of the body 112. As shown in FIG. 3, the second valve 128 may extend distally from the proximal portion 114 of the body 112. In other embodiments, the second valve 128 may extend from any portion of the body 112. In some embodiments, the distal end 136 of the second valve 128 is proximal to a proximal end 152 of the first valve 126. In some embodiments, the first valve 126 may extend from the proximal portion 114 of the body 112 and distal to the distal portion 116 of the body 112. The second valve 128 may extend within a lumen 132 of the first valve 126 extending from the proximal portion 114 and be positioned entirely within the body 112.

The second valve 128 includes a lumen 138 that is operably connected to the lumen 118 of the body 112. The lumen 132 of the first valve 126 is also operably connected to the lumen 118 of the body 112 so that flow of liquid and nutrients can pass from the mouth to the stomach. A distal end portion 142 of the first valve 126 is normally closed in response to the first pressure 44 so that the distal end portion 142 collapses on itself in the absence of flow from the mouth to the stomach. A distal end portion 146 of the second valve 128 may also be normally closed in response to the first pressure 44 so that the distal end portion 146 collapses on itself. The first valve 126 and the second valve 128 cooperatively prevent leakage of stomach contents through the prosthesis 100 in response to the first pressure 44, especially when the patient is in a prone position. In response to the second pressure 48 that is greater than the first pressure 44, the first and second distal end portions 142, 146 open to allow liquids and nutrients to flow from the mouth to the stomach in the first direction 49 (shown in FIG. 10). Once the contents have passed from the mouth to the stomach, the first valve 126 and in some embodiments, the second valve 128, return to the closed position 55. In response to the third pressure 50, the second valve 128 inverts and the first valve 126 inverts to relieve the third pressure 50 as described in more detail below. The first valve 126 may be sized and shaped so that when the first valve 126 and the second valve 128 invert and open in response to the third pressure 50, the first valve 126 does not contact the second valve 128.

Figure 4:
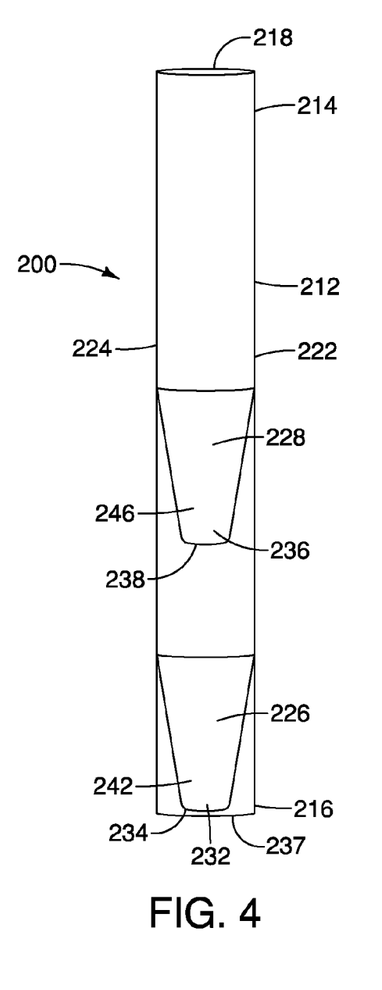
FIG. 4 is a side sectional view of an embodiment of a prosthetic device having a first valve and a second valve.

FIG. 4 illustrates an embodiment of a prosthesis 200. The prosthesis 200 includes a body 212 having proximal portion 214, a distal portion 216 and a lumen 218 extending therethrough. Similar to the prosthesis 10 described above, the prosthesis 200 may include an expandable or a non-expandable stent. The body 212 may include a coating or a sleeve 222 extending through or around the body 212 that is liquid impermeable so that liquid and nutrients flowing from the proximal portion 214 to the distal portion 216 or stomach contents from the distal portion 216 to the proximal portion 214 do not pass through a wall 224 of the body 212. The prosthesis 200 includes a first valve 226 and a second valve 228. In some embodiments, first valve 226 and the second valve 228 may be provided as flexible sleeves.

As shown in FIG. 4, a distal end of the first valve 226 and a distal end of the second valve 228 extend distally toward the distal portion 216 of the body 212. The first valve 226 and the second valve 228 may be positioned within the body 212 of the prosthesis 200 so that the distal ends 234, 236 are both proximal to a distal end 237 of the body 212. As shown in FIG. 4, the second valve 228 extends distally from the body 112 and is positioned proximal to the first valve 226. In some embodiments, the second valve 228 is spaced apart from the first valve 226. In some embodiments, the second valve 228 may extend at least partially within a lumen 232 of the first valve 226.

Similar to the embodiments described above, the second valve 228 includes a lumen 238 that is operably connected to the lumen 218 of the body 112. The lumen 232 of the first valve 226 is also operably connected to the lumen 218 of the body 212 so that fluids and nutrients can flow from the mouth to the stomach. A distal end portion 242 of the first valve 226 is normally closed in response to the first pressure 44 so that the distal end portion 242 collapses. A distal end portion 246 of the second valve 228 may also be normally closed in response to the first pressure 44 so that the distal end portion 246 collapses on itself. The first valve 226 and the second valve 228 cooperatively prevent leakage of stomach contents through the prosthesis 200 in response to the first pressure 44, especially when the patient is in a prone position. In response to the second pressure 48 that is greater than the first pressure 44, the first and second distal end portions 242, 246 open to allow liquids and nutrients to flow from the mouth to the stomach. Once the contents have flowed from the mouth to the stomach, the first valve 226 and in some embodiments, the second valve 228, return to the closed position. In response to the third pressure 50, the second valve 228 inverts and the first valve 226 inverts to relieve the third pressure 50 as described in more detail below. The first valve 226 may be sized and shaped so that when the first valve 226 and the second valve 228 invert and open in response to the third pressure 50, the first valve 226 does not contact the second valve 228.

Figure 5:
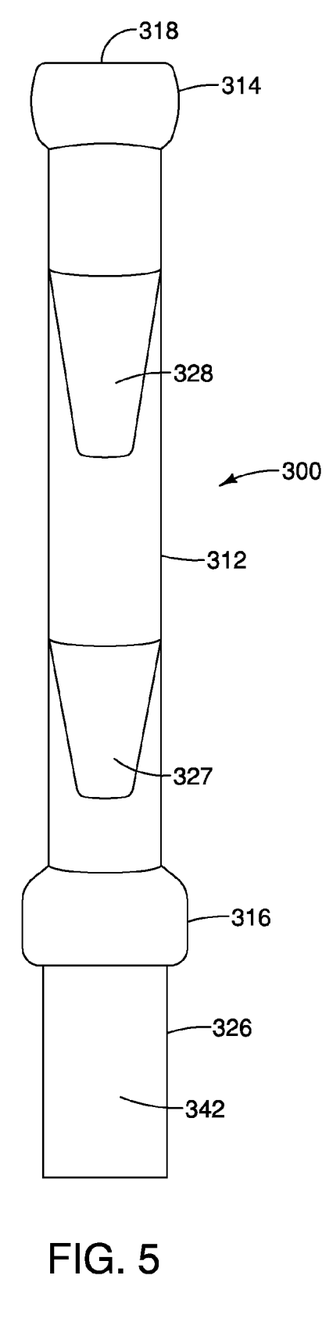
FIG. 5 is a side sectional view of an embodiment of a prosthetic device having a first valve, a second valve and a third valve.

FIG. 5 illustrates an embodiment of a prosthesis 300. The prosthesis 300 is similar to the embodiments described above and additionally includes a third valve 327 positioned between a first valve 326 and a second valve 328. The prosthesis 300 includes a body 312 having proximal portion 314, a distal portion 316 and a lumen 318 extending therethrough. The valves 326, 327, 328 respond to the first, second and third pressures 44, 48, 50 similar to the embodiments discussed above. The prosthesis 300 is normally closed in response to the first pressure 44 with at least a distal end 342 of the first valve 326 collapsed on itself in the presence of the first pressure 44. The first valve 326, the second valve 328 and the third valve 327 cooperatively prevent leakage of stomach contents through the prosthesis 300 in response to the first pressure 44, especially when the patient is in a prone position. The prosthesis is normally open in response to the second pressure 48 so that liquids and nutrients can flow from the mouth to the stomach through the prosthesis 300. The prosthesis 300 is normally open in response to the third pressure 50 wherein the valves 326, 327 and 328 invert to allow the patient to belch or vomit.

Figure 6:
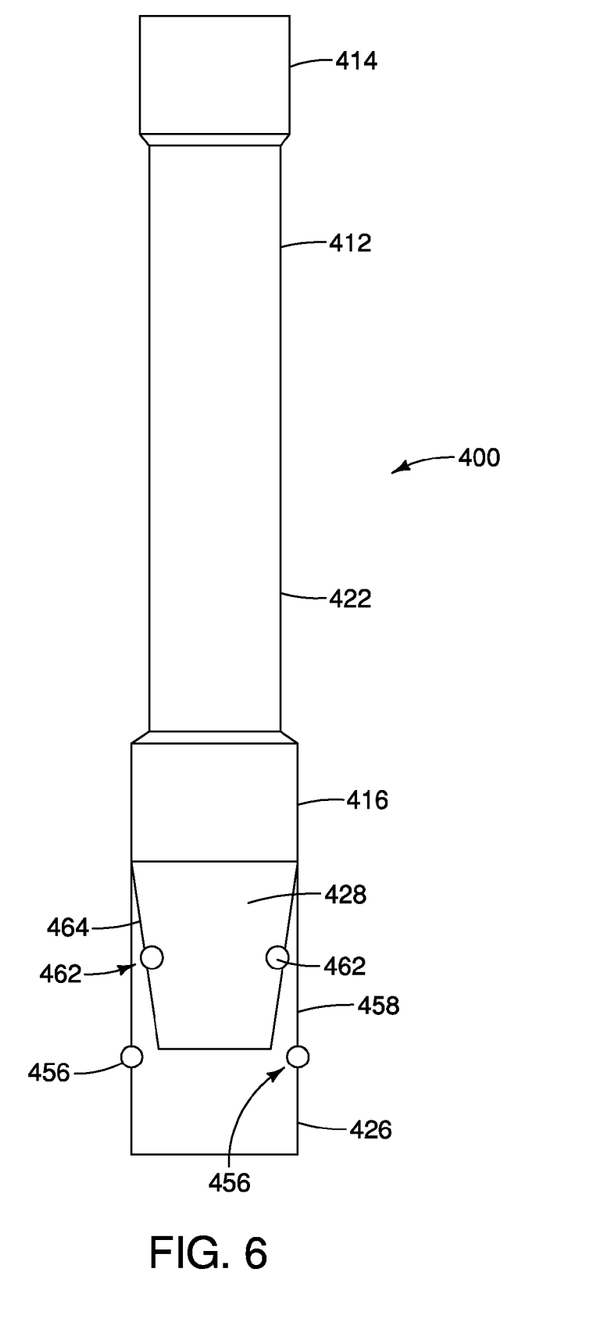
FIG. 6 is a side view of an embodiment of a prosthetic device having a first valve and a second valve.

FIG. 6 illustrates a prosthesis 400 in accordance with an embodiment of the present invention. The prosthesis 400 includes a body 412 having proximal portion 414, a distal portion 416 and a lumen 418 extending therethrough. Similar to the embodiments described above, the body 412 may be an expandable or a non-expandable stent. The body 412 may include a coating or a valve 422 extending through or around the body 412 that is liquid impermeable. In some embodiments, the prosthesis 400 includes a first valve 426 and a second valve 428. The first valve 426 may be contiguous with the coating or sleeve 422 and in some embodiments the first valve 426 may be separately provided. In some embodiments, the first valve 426 and the second valve 428 may be provided as flexible sleeves As shown in FIG. 6, the first valve 426 may include one or more openings 456 through a wall 458 of the first valve 426. The openings 456 may facilitate drainage for any leaks through the prosthesis 400 so that the contents may be returned to the stomach. The second valve 428 may include one or more openings 462 through a wall 464 of the second valve 428. The openings 462 facilitate drainage for any leaks through the prosthesis 400 so that the contents may be returned to the stomach. The openings 462 may be offset from the openings 456 to prevent leakage from the stomach to the mouth, for example while the patient is in a prone position. The prosthesis 400 is similar to the embodiments shown above and responds to the first, second and third pressures 44, 48, 50 such that the prosthesis 400 remains closed in response to the first pressure 44 and is open in response to the second and third pressures 48, 50.

Figure 7:
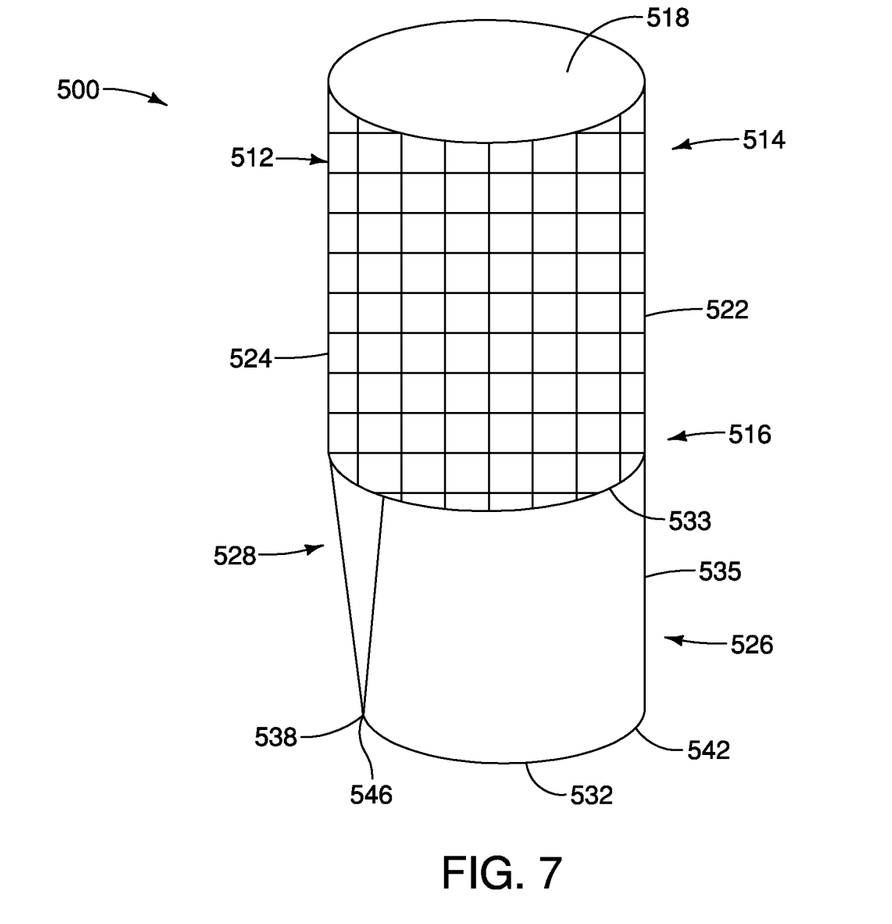
FIG. 7 is a side view of an embodiment of a prosthetic device having a first valve and a second valve.

FIG. 7 illustrates an embodiment of a prosthesis 500. The prosthesis 500 includes a body 512 having proximal portion 514, a distal portion 516 and a lumen 518 extending therethrough. Similar to the prosthesis 10 described above, the prosthesis 500 may include an expandable or a non-expandable stent. The body 512 may include a coating or a sleeve 522 extending through or around the body 512 that is liquid impermeable so that liquid and nutrients flowing from the proximal portion 514 to the distal portion 516 or stomach contents from the distal portion 516 to the proximal portion 514 do not pass through a wall 524 of the body 512. The prosthesis 500 includes a first valve 526 and a second valve 528.

The first valve 526 and the second valve 528 may be configured to respond to different pressures when placed within a body lumen. In some embodiments, the prosthesis may include a non-inventing first valve 526 and an inventing second valve 528. Similar to the embodiments described above, the second valve 528 includes a lumen 538 that is operably connected to the lumen 518 of the body 512. A lumen 532 of the first valve 526 is also operably connected to the lumen 518 of the body 512 so that fluids and nutrients can flow from the mouth to the stomach. A distal end portion 542 of the first valve 526 may be normally closed. A distal end portion 546 of the second valve 528 may also be normally closed. The first valve 526 and the second valve 528 cooperatively prevent leakage of stomach contents through the prosthesis 500 in response to the first pressure 44, especially when the patient is in a prone position. In response to the second pressure 48 that is greater than the first pressure 44, the first and second distal end portions 542, 546 may open to allow liquids and nutrients to flow from the mouth to the stomach. Once the contents have flowed from the mouth to the stomach, the first valve 526 and in some embodiments, the second valve 528, return to the closed position. In response to the third pressure 50, the second valve 528 inverts to relieve the third pressure 50 and the first valve 526 does not invert. The first valve 526 may be configured to allow the passage of food and fluid to the stomach. The first valve 526 may be configured to form a shape that creates a protective barrier against reflux/aspiration at low pressures. A portion 533 of the first valve 526 may be attached to the body 512 and/or include a support structure 535 attached to the body 512 to prevent the first valve 526 from inverting. In some embodiments, the first valve 526 may have a thickness that would prevent the first valve 526 from inverting from inverting. For example, the thickness of the first valve 526 may be greater than about 0.6 mm. As shown in FIG. 7, the non-inverting first valve 526 may be larger than the inverting second valve 528.

As shown in FIG. 7, the prosthesis 500 may include the second valve 528 positioned outside the first valve 526 and connected to the body 512. The second valve 528 may be configured to allow the patient to belch or vomit in response to the increased pressure 50 within the stomach. The second valve 528 may have a smaller diameter than the first valve 526. In some embodiments the ratio of the diameter of the second valve 528 to the diameter of the first valve 526 is a ratio of about 1:4. By way of non-limiting example, the diameter of the first valve may be about 15-35 mm. The diameter of the second valve 528 may be about 2.0-15 mm. The second valve 528 may be shorter, equal to or longer than the first valve 526. In some embodiments, the first valve 528 may have a length of about 0.5 cm to about 5 cm. The second valve 528 may have a length of about 0.5 cm to about 4 cm.

In some embodiments, the prosthesis 500 may include the first non-inverting vale 526, the second inverting valve 528 and a third inventing valve (not shown). The third inventing valve may be sized and shaped similarly to the second inverting valve 528.

The materials used to manufacture the components of the prosthetic devices described herein may be any materials known to one skilled in the art that are suitable for use in patients. By way of non-limiting example, the body may be formed from metals or polymers. Suitable exemplary metals include stainless steel and nitinol and the body may be woven or provided in a zig-zag configuration. Valves of the prosthetic devices of the embodiments may be made from any suitable biocompatible material that is liquid impermeable and that does not degrade in the presence of fluids or gastric material that comes in contact therewith. By way of non-limiting example, the valve may be made from a medical grade polyurethane material, silicone, nylon, polyamides such as other urethanes, polyethylene, polyethylene terephthalate (PET), polystyrene-ethylene (PSE), polytetrafluoroethylene (PTFE), ultrahigh molecular weight, low density and high density polyethylene, elastomeric polyethylene, polyethyleneoxide (PEO), block copolymers containing polystyrene and poly(1,4-butadiene), ABA triblock copolymer made from poly(2-methyl-2-oxazoline), polytetrahydrofuran, shape memory polymers, amorphous or organic-inorganic hybrid polymers containing polymorbornere units or other biocompatible materials that are flexible and acid resistant. In some embodiments, portions of the valve may be made from biodegradable materials such as PLA, PLGA, PBA or nitinol. An exemplary material for the valve is a medical grade polyurethane material grade EG-80A material commercially known as TECOFLEX® polyurethane material (Thermedics, Incorporated, Woburn, Mass.).

The first valve and the second valve of the embodiments described above may be made from the same or different materials. In some embodiments, the first valve or a portion thereof may be made of a heavier gauge material relative to the second valve. The first valve may be configured to be stiffer than the second valve so that the second valve inverts more readily in response to the third pressure than the first valve. The first valve may be made stiffer by providing a material having a greater thickness relative to the first valve. In some embodiments, the first valve may have a different shape than the second valve so that the second valve inverts more readily than the first valve in response to the third pressure. In some embodiments, the first valve and the second valve may be made from the same material and have the same stiffness so that both the first and the second valve invert in response to the same third pressure. The third valve, when present, may be the same as the first valve, the second valve or both or may be different than both the first valve and the second valve.

In some embodiments, the length of the first valve extending from the distal end of the body of the prosthesis may be from about 0 cm to about 20 cm, from from about 5 cm to about 15 cm and from about 8 cm to about 12 cm. The length may vary and will depend on anatomy of the patient. In some embodiments, the thickness of the first and second valves may be from about 0.1 mm to about 3.0 mm. In some embodiments, the distal end portions of the first and second valves may be about 0.05 mm to about 0.15 mm while the remainder of the each valve has a greater thickness. In some embodiments, the thickness of the distal end portion of the first valve may be greater than the thickness of the distal end portion of the second valve.

Operation of the prosthesis will be explained with reference to the prosthesis 10 as an example. Operation of the prosthesis 10 is shown in FIGS. 1A and 8-12. The prosthesis 10 may be delivered to the LES using a delivery catheter (not shown) and positioned in the LES so that the proximal portion 14 of the body 12 is positioned above the sphincter 11 and the distal portion 16 of the body 12 is positioned in the stomach 13. (See FIG. 2.) The first valve 26 and the second valve 28 may be delivered to the LES with the first valve 26 and the second valve 28 positioned within the lumen 18 of the body 12 or extending distally with the first valve extending distally from the distal portion 16 of the body 12. When the first and second valves 26, 28 are delivered within the lumen 18 of the body 12 to the LES, the valves 26, 28 may be distally extended after positioning the body 12 in the sphincter by having the patient drink a liquid so that the second pressure 48 is applied and the valves 26, 28 open and extend distally.

FIG. 1A illustrates the prosthesis 10 in a closed configuration 55 with the first and second valves 26, 28 extending distally and the prosthesis 10 is closed so that gastric contents under the first pressure 44 are prevented from flowing from the stomach 13 to the mouth of the patient. The first valve 26 is collapsed upon itself at the distal end portion 42. The prosthesis 10 also has an open configuration 57 shown in FIGS. 11 and 12 where the lumen 32 of the first valve 26 and the lumen 38 of the second valve 28 are open in response to the second pressure 48 so that liquids and nutrients can flow through the prosthesis 10 from the mouth to the stomach 13.

Figure 8:
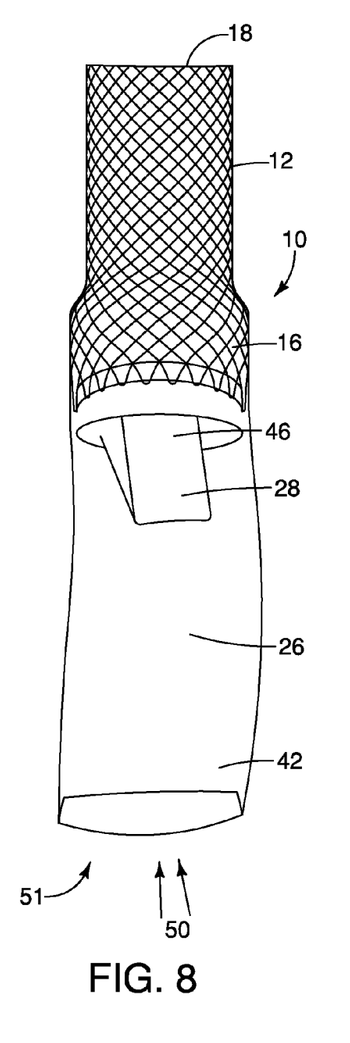
FIGS. 8-11 illustrate operation of an embodiment of a prosthetic device.
Figure 9:
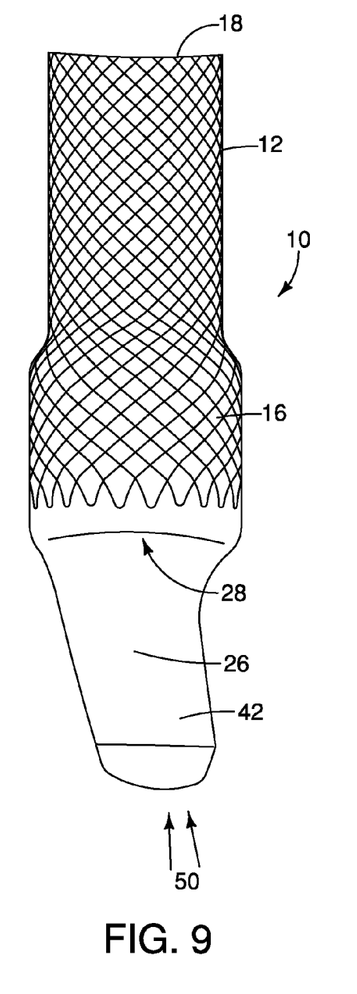
Figure 10:
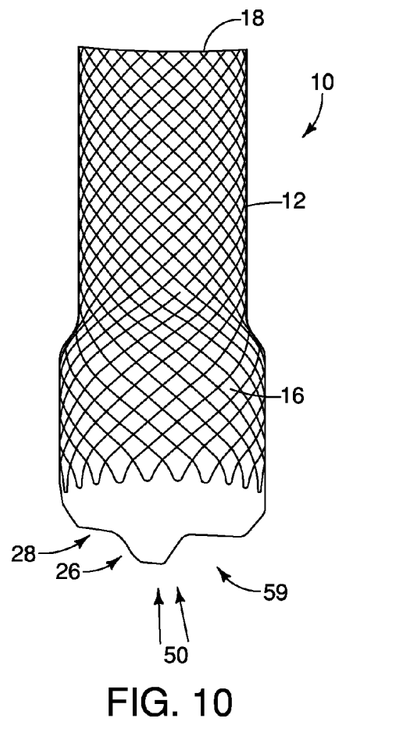
Figure 11:
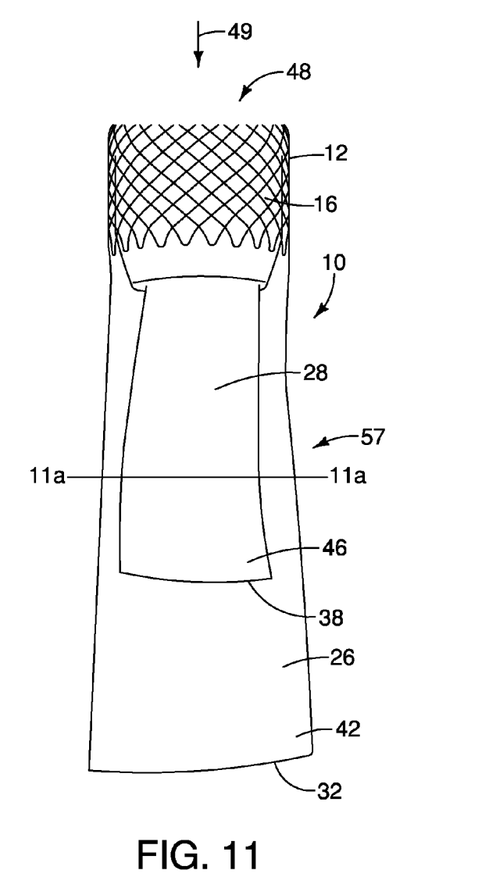
Figure 12:
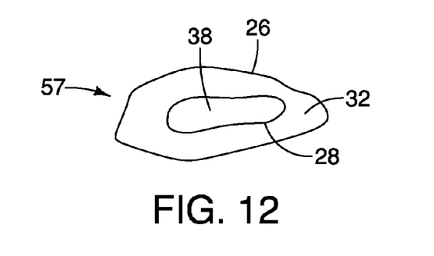
FIG. 12 is a cross sectional view across line 11-11 shown in FIG. 11.

As discussed above, the first and second valves of the prosthesis in certain embodiments may invert at different rates in response to the third pressure 50 depending on the materials, shapes and thicknesses of the first and second valves relative to each other. FIGS. 8-10 illustrate an embodiment of the prosthesis 10 inverting in response to the third pressure 50. As shown in FIG. 8, the second valve 28 of the prosthesis 10 may invert in response to the third pressure 50 more readily than the first valve 26. The second valve 28 is shown with the distal end portion 46 of the second valve 28 inverting into the lumen 18 of the body 12. The first valve 26 is shown with the distal end portion 42 of the first valve 26 extending distally from the distal portion 16 of the body 12 while the second valve 28 inverts. FIG. 9 illustrates the second valve 28 completely inverted and extending proximally through the lumen 18 of the body 12 so that the lumen 38 of the second valve 28 is open. The first valve 26 is shown beginning to invert in response to the third pressure 50 so that the distal end portion 42 moves proximally toward the lumen 18 of the body 12.

FIG. 10 illustrates both the first valve 26 and the second valve 28 inverted into the lumen 18 of the body 12 in an inverted configuration 59. In the inverted configuration 59, the distal end portions 42, 46 of the first and second valves 26, 28 are extended proximally into the lumen 18 of the body 12 and the lumens 32, 38 of the first and second valves 26, 28 are open in response to the third pressure 50 so that the patient can belch or vomit. Once the third pressure 50 is relieved, the first and second valves 26, 28 may be re-inverted so that the distal end portions 42, 46 of the first and second valves 26, 28 extend distally from the body 12 of the prosthesis 10. As discussed above, the prosthesis 10 may be returned to the open configuration 57 by the patient swallowing a liquid to provide the second pressure 48. The prosthesis 10 may then be closed and remain in the closed configuration 55 (shown in FIG. 1A) in the presence of the first pressure 44.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A prosthesis for controlling flow through a bodily lumen, the prosthesis comprising:
 a body having a proximal portion, a distal portion and a lumen extending therethrough;
 a first valve operably connected to the body, the first valve having a proximal portion, a distal portion, a distal end extending distally relative to the proximal portion of the body and a lumen extending through the first valve, the first valve being closed in an absence of a second pressure in a first direction and a third pressure in a second direction that are greater than a first pressure, the third pressure being greater than the second pressure; and
 a second valve operably connected to the body, the second valve having a proximal portion, a distal portion, a distal end extending distally relative to the proximal portion of the body in a first configuration of the second valve and a lumen extending through the second valve, the distal end of the first valve extending distal to the distal end of the second valve, the distal end of the first valve extends distal to a distal end of the body in a first configuration of the first valve, the first valve being closable on itself so that walls of the first valve defining the first valve lumen contact each other at the distal portion and the distal end of the first valve when the first valve is closed and extending distal to the distal end of the body, the second valve is an inverting valve wherein the distal end of the second valve extends proximally in a second, inverted configuration of the second valve in response to the third pressure, the second valve and the first valve controlling flow through the prosthesis to allow flow in the first direction and the second direction through the prosthesis in response to the second pressure and the third pressure.

2. The prosthesis of claim 1, wherein at least a portion of the second valve extends distally within the lumen of the first valve.

3. The prosthesis of claim 1, wherein the second valve is spaced apart from first valve so that the distal end of the second valve is proximal to a proximal end of the first valve.

4. The prosthesis of claim 1, wherein the proximal portion of the first valve comprises a sleeve disposed about the body.

5. The prosthesis of claim 1, wherein the second valve is closed in the absence of the second and the third pressure.

6. The prosthesis of claim 1, wherein the distal portion of the second valve is positioned entirely within the body.

7. The prosthesis of claim 1, wherein the first valve, the second valve or both comprise at least one hole extending therethrough.

8. The prosthesis of claim 1, wherein the distal portion of the first valve and the distal portion of the second valve have different thicknesses.

9. The prosthesis of claim 1, wherein at least of portion of the first valve and at least a portion of the second valve are formed from different materials.

10. The prosthesis of claim 1, further comprising a third valve positioned between the first valve and the second valve.

11. The prosthesis of claim 1, wherein the first valve is a non-inverting valve.

12. The prosthesis of claim 1, wherein the first valve comprises a sleeve of flexible material.

13. The prosthesis of claim 1, wherein the distal end of the first valve and the distal end of the second valve extend distal to a distal end of the body.

14. The prosthesis of claim 1, wherein the second valve is connected to the first valve to operably connect to the body.

15. The prosthesis of claim 1, wherein the distal end of the first valve and the distal end of the second valve are proximally extendable in response to the third pressure that is greater than the first pressure and the second pressure.

16. The prosthesis of claim 2, wherein the body comprises a woven material and the distal end of the first valve and the distal end of the second valve extend distal to the woven material.

17. A prosthesis for controlling flow through a bodily lumen, the prosthesis comprising:
a body comprising a stent having a proximal portion, a distal portion, a distal end, and a lumen extending therethrough;
a first valve operably connected to the stent, the first valve having a proximal portion, a distal portion, a distal end extending distally relative to the proximal portion of the stent and a lumen extending through the first valve, the first valve being closed in an absence of a second pressure in a first direction and a third pressure in a second direction that are greater than a first pressure, the third pressure being greater than the second pressure; and
a second valve operably connected to the stent, the second valve having a proximal portion, a distal portion, a distal end extending distally relative to the proximal portion of the stent in a first configuration of the second valve and a lumen extending through the second valve, the distal end of the first valve extending distal to the distal end of the second valve in a first configuration of the first valve, the distal end of the first valve and the distal end of the second valve extending distal to a distal end of the stent in a first configuration of the first valve and the second valve, the second valve is an inverting valve wherein the distal end of the second valve extends proximally in a second, inverted configuration of the second valve in response to the third pressure.

18. A prosthesis for controlling flow through a bodily lumen, the prosthesis comprising:
a body having a proximal portion, a distal portion and a lumen extending therethrough;
a first valve operably connected to the body, the first valve having a proximal portion, a distal portion, a distal end extending distally relative to the proximal portion of the body and a lumen extending through the first valve, the first valve being closed in an absence of a second pressure in a first direction and a third pressure in a second direction that are greater than a first pressure, the third pressure being greater than the second pressure; and
a second valve operably connected to the body, the second valve having a proximal portion, a distal portion, a distal end extending distally relative to the proximal portion of the body and a lumen extending through the second valve, the distal end of the first valve extending distal to the distal end of the second valve, the distal end of the first valve extends distal to a distal end of the body, the first and second valves are inverting valves wherein the distal end of the first valve and the distal end of the second valve extend proximally in response to the third pressure, wherein the first and second valves invert at different rates.

19. The prosthesis of claim 18, wherein the first and second valves comprise different materials, different shapes or different thicknesses.

\* \* \* \* \*

UNITED STATES PATENT AND TRADEMARK OFFICE
CERTIFICATE OF CORRECTION

PATENT NO. : 9,526,605 B2
APPLICATION NO. : 14/149104
DATED : December 27, 2016
INVENTOR(S) : Gerard Treacy et al.

Page 1 of 1

It is certified that error appears in the above-identified patent and that said Letters Patent is hereby corrected as shown below:

In the Claims

In Column 11, Claim 9, Line 16, after "wherein at least" replace "of portion of" with --a portion of--.

Signed and Sealed this
Ninth Day of January, 2018

Joseph Matal
*Performing the Functions and Duties of the*
*Under Secretary of Commerce for Intellectual Property and*
*Director of the United States Patent and Trademark Office*